United States Patent [19]

Balnave

[11] Patent Number: 4,498,945

[45] Date of Patent: Feb. 12, 1985

[54] METHOD AND MEANS FOR SPOOLING TUBING

[75] Inventor: Peter Balnave, Glen Rock, N.J.

[73] Assignee: Kahle Engineering Company, Union City, N.J.

[21] Appl. No.: 556,967

[22] Filed: Dec. 1, 1983

[51] Int. Cl.³ .............................................. B29B 3/00
[52] U.S. Cl. .................................... 156/256; 156/294; 156/517; 156/556
[58] Field of Search ............... 156/515, 510, 294, 521, 156/556, 204, 443, 559, 256, 516–517; 226/104–107

[56] References Cited

U.S. PATENT DOCUMENTS

| | | | |
|---|---|---|---|
| 3,867,873 | 2/1975 | Simpson | 156/515 X |
| 3,971,299 | 7/1976 | Whittle et al. | 156/515 X |
| 4,244,772 | 1/1981 | Achelpohl | 156/515 |
| 4,345,963 | 8/1982 | Braber | 156/294 X |

Primary Examiner—David Simmons
Attorney, Agent, or Firm—Stoll, Wilkie, Previto & Hoffman

[57] ABSTRACT

A method and means are disclosed for removing a predetermined length of tubing from the end of a roll of tubing and for thereafter controlling the two free ends of the cut tube for attachment to tube end fixtures.

12 Claims, 11 Drawing Figures

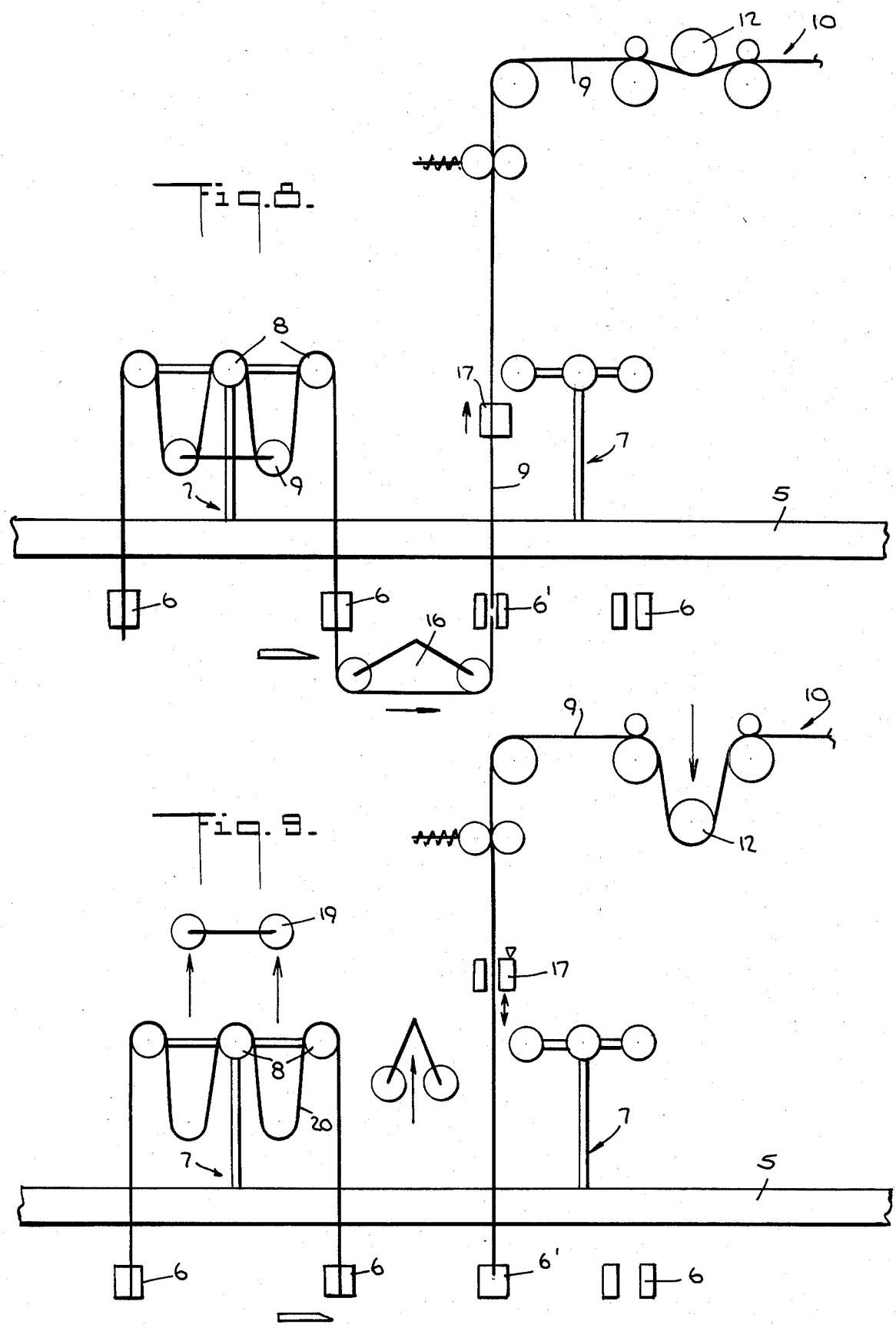

METHOD AND MEANS FOR SPOOLING TUBING

BACKGROUND OF THE INVENTION

The present invention relates to a method and means for automatically handling tubing and more particularly to a method and means for removing a short length of tubing from a roll of tubing and for controlling the two free ends of the tube for attachment to an end fixtures.

There are a number of uses for lengths of tubing, such as plastic tubing, having molded plastic or other fixtures attached to the opposite ends of the tubing. Such assemblies, for example, are used in great numbers in medicine and particularly in connection with fluid administration apparatus for intravenous feeding or administering blood or similar procedures.

FIG. 11 illustrates an assembly of this general type comprising a short plastic tube with end fixture attached to the opposite ends. These assemblies or sets have previously been assembled by hand or in a semi-automatic manner using some fixtures. The method and means of the present invention replace these operations with an automatic operation which may be run with minimal supervision for producing complete sets accurately and at high speeds.

Accordingly, an object of the present invention is to provide an improved method and means for cutting lengths of tubing from a roll of tubing and for controlling the free ends incident to the attachment to end fixtures.

Another object of the present invention is to provide automatic means for cutting pre-determined lengths of tubing from tubing rolls and for controlling the opposite ends of the cut lengths.

Other and further objects of the present invention will become apparent upon an understanding of the illustrative embodiments about to be described, or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification, wherein:

FIGS. 2 through 10 are diagramatic views illustrating the successive steps for performing the method of the invention.

Figure 11:
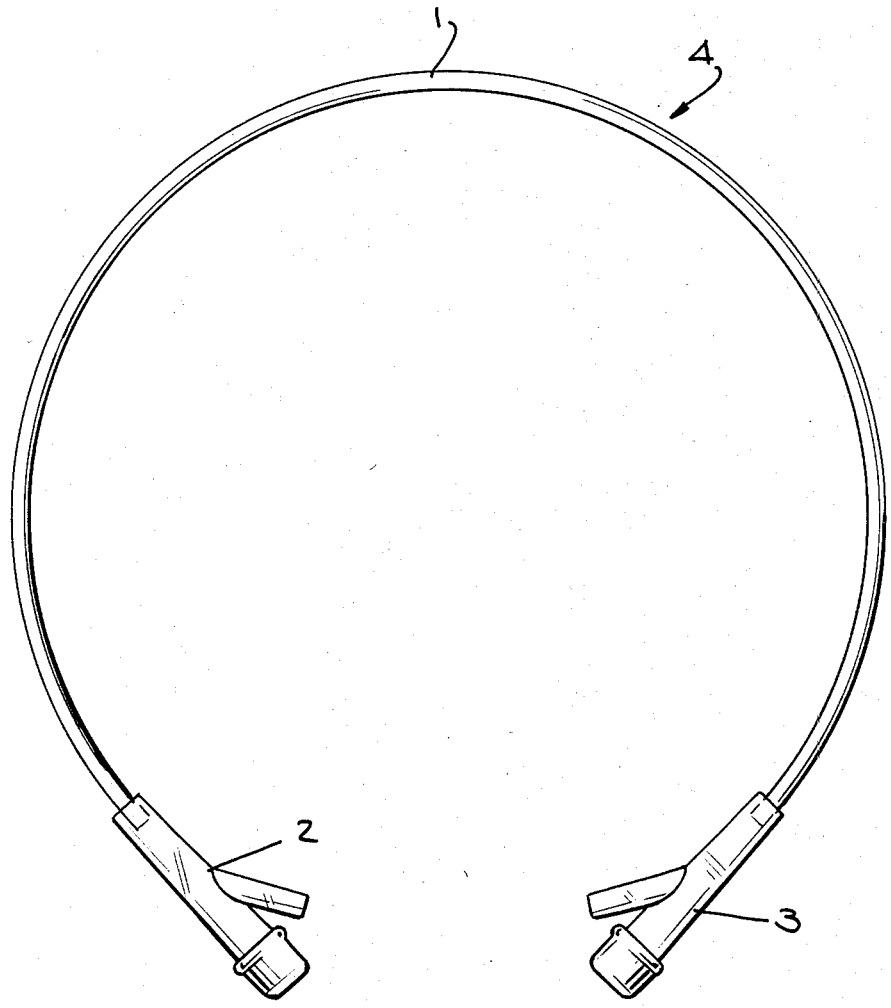
FIG. 11 is a side elevational view of a typical tube set formed by the method and means of the invention.

A typical medical fluid administration set is illustrated in FIG. 11 comprising plastic tube 1 which is cut to a pre-determined length and having molded plastic fixtures 2 and 3 attached to the opposite ends of the tube 1. The particular set 4 illustrated is not part of the invention and reference is made to it for the purpose of describing the method and means of the invention wherein tube 1 is cut from a roll of tubing and the free tube ends are handled incident to the attachment of the fixtures 2 and 3 to the opposite ends.

Figure 1:
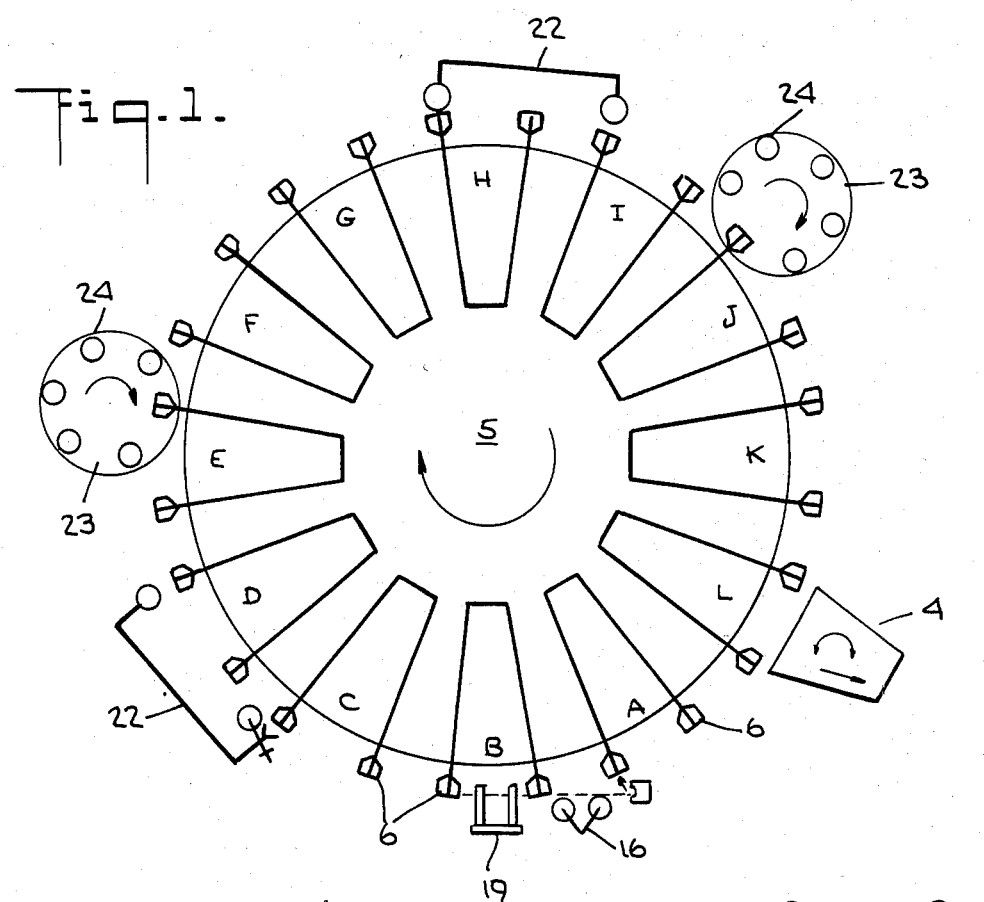
FIG. 1 is a diagramatic plan view of a spooling means in accordance with the present invention.

The method as described herein is suited for use on the well-known indexing or rotating turret type product assembly machines wherein a series of work stations on the moving turret are moved past a circular array of stationary work stations positioned around the circumference of the turret. Such turrets and the means for rotating them at pre-determined speeds or in indexing movements are well known. The turret 5 illustrated in FIG. 1 has twelve spaced work stations A-L on the turret, each including spaced clamps 6 for releasably gripping opposite ends of a length of tubing 1 and a vertically mounted tube support 7 comprising three spaced roller elements 8 for supporting a tube 1 as will be further described below. The tubing 9 is fed to the turret 5 from a roll of tubing (not shown) at a feed station illustrated generally at 10 in FIG. 2. The tubing 9 is supplied from a large roll and passes over spaced rollers 11-14 including a vertically reciprocating slack producing roller 12. The roller 14 directs the tubing 9 downwardly through a pair of pinch rollers 15 and past a tube feeder assembly 16 and an open lift clamp 17 to one of the clamps 6 provided at station A on the turret 5.

Figure 2:
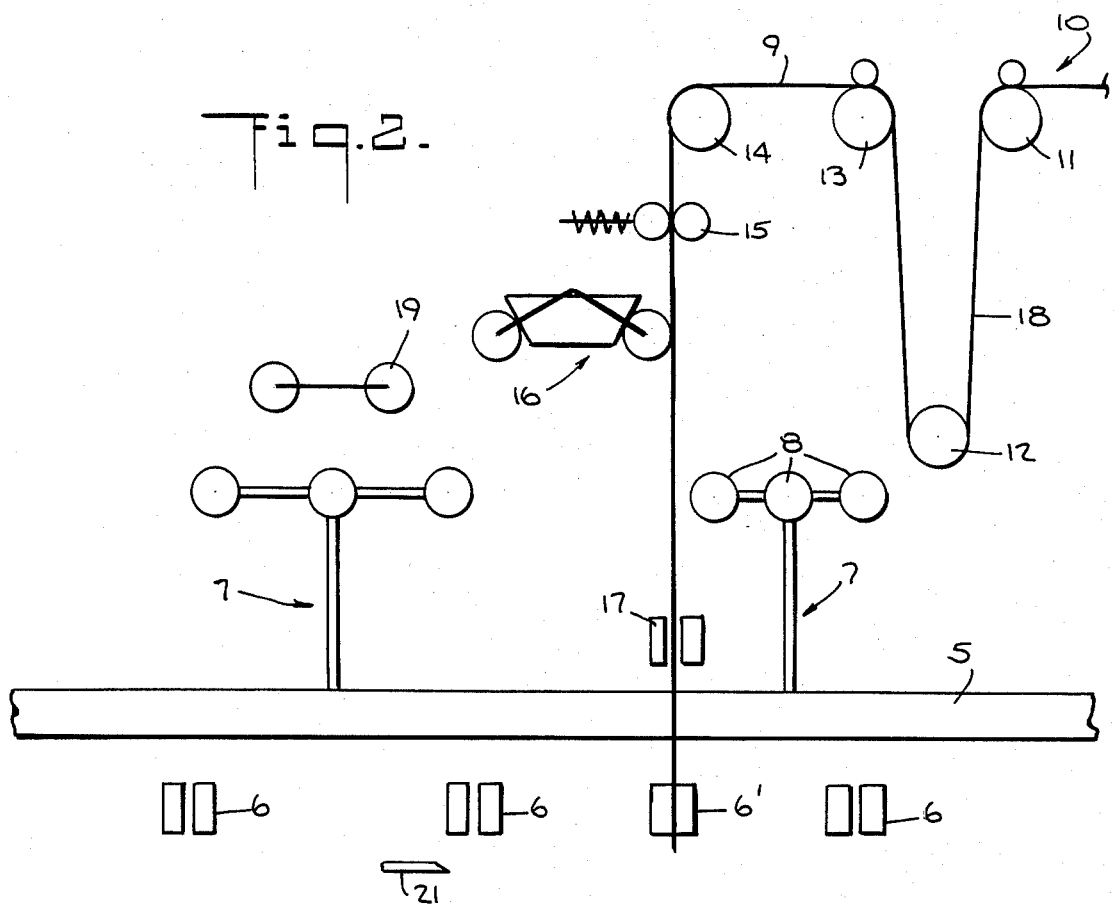
Figure 3:
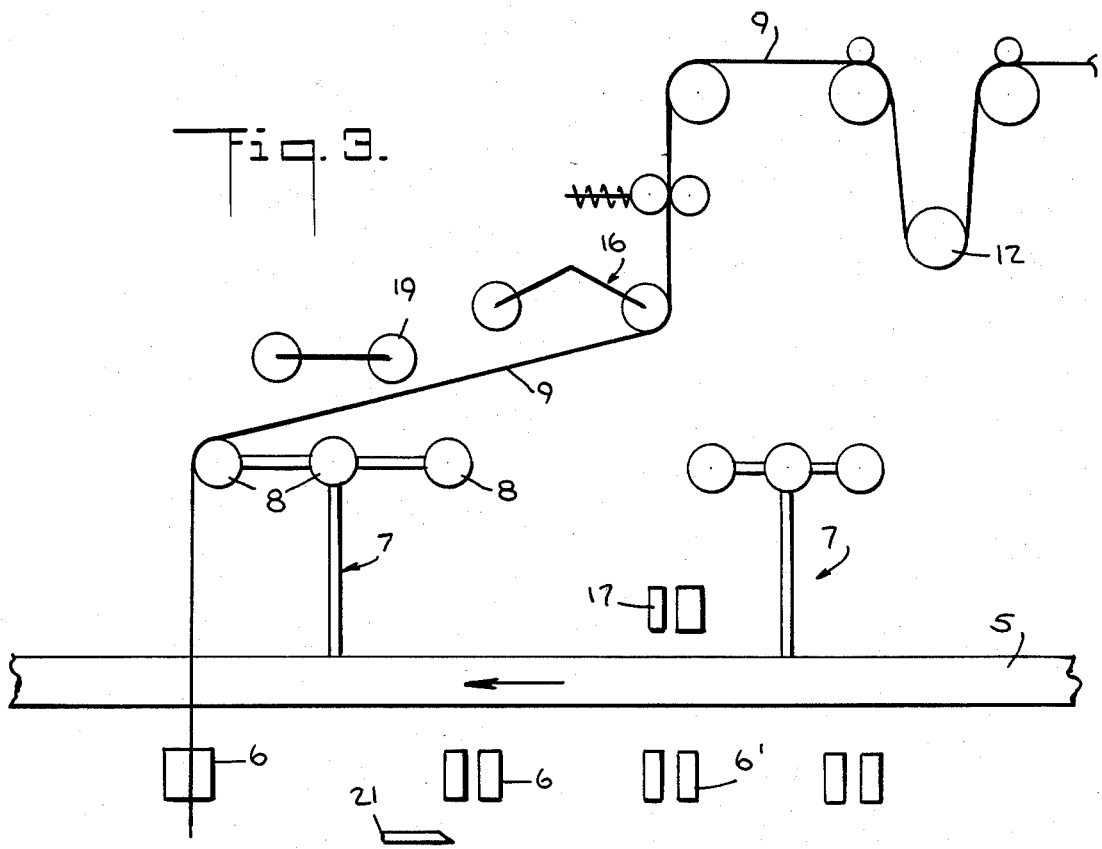
Figure 4:
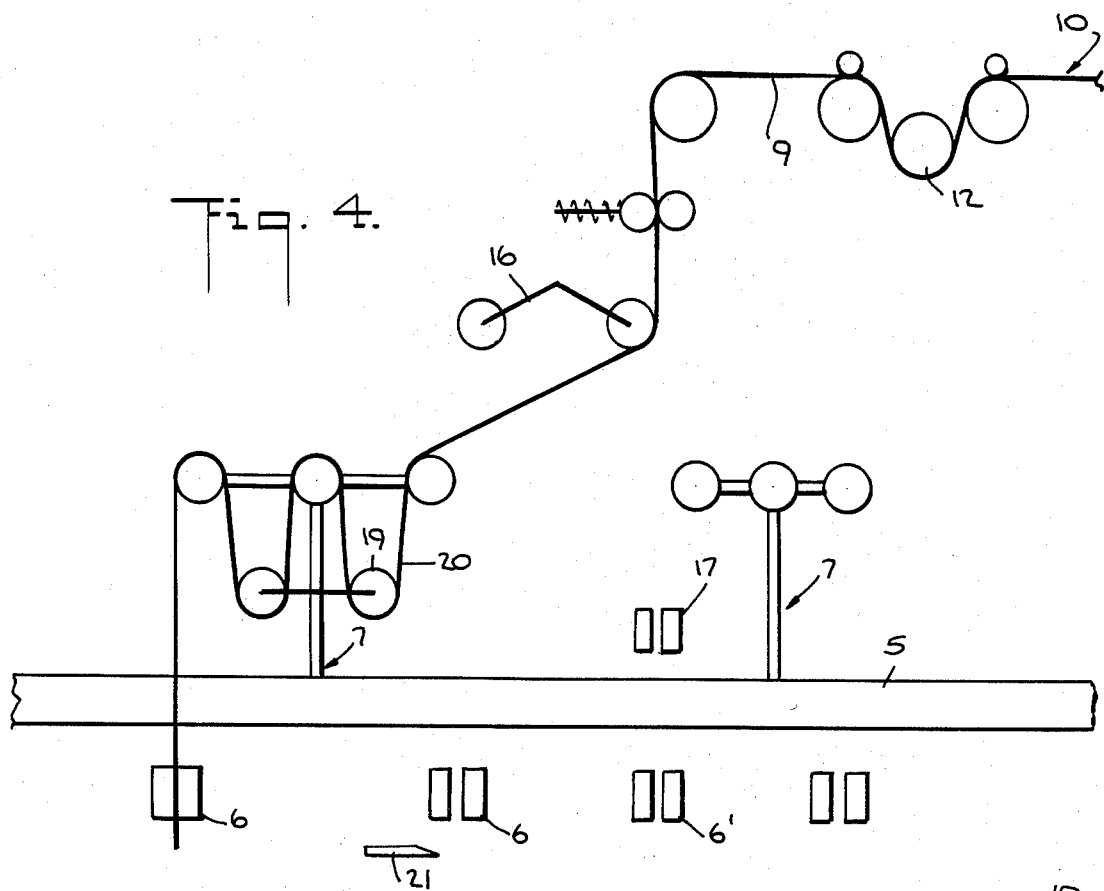

FIG. 2 illustrates the position of the tube 9 with respect to the above described elements at the completion of the prior tube cutting cucle which will now be further described with reference to FIGS. 3 through 10.

With the tube 9 in this position, the turret 5 is stepped to the next station (FIG. 3) drawing tubing 9 from the slack portion 18 provided by the slack roller 12. A pair of looping rollers 19 next move downwardly (FIG. 4) to form loops of slack 20 between the three spaced rollers 8 of the spool assembly 7.

Figure 5:
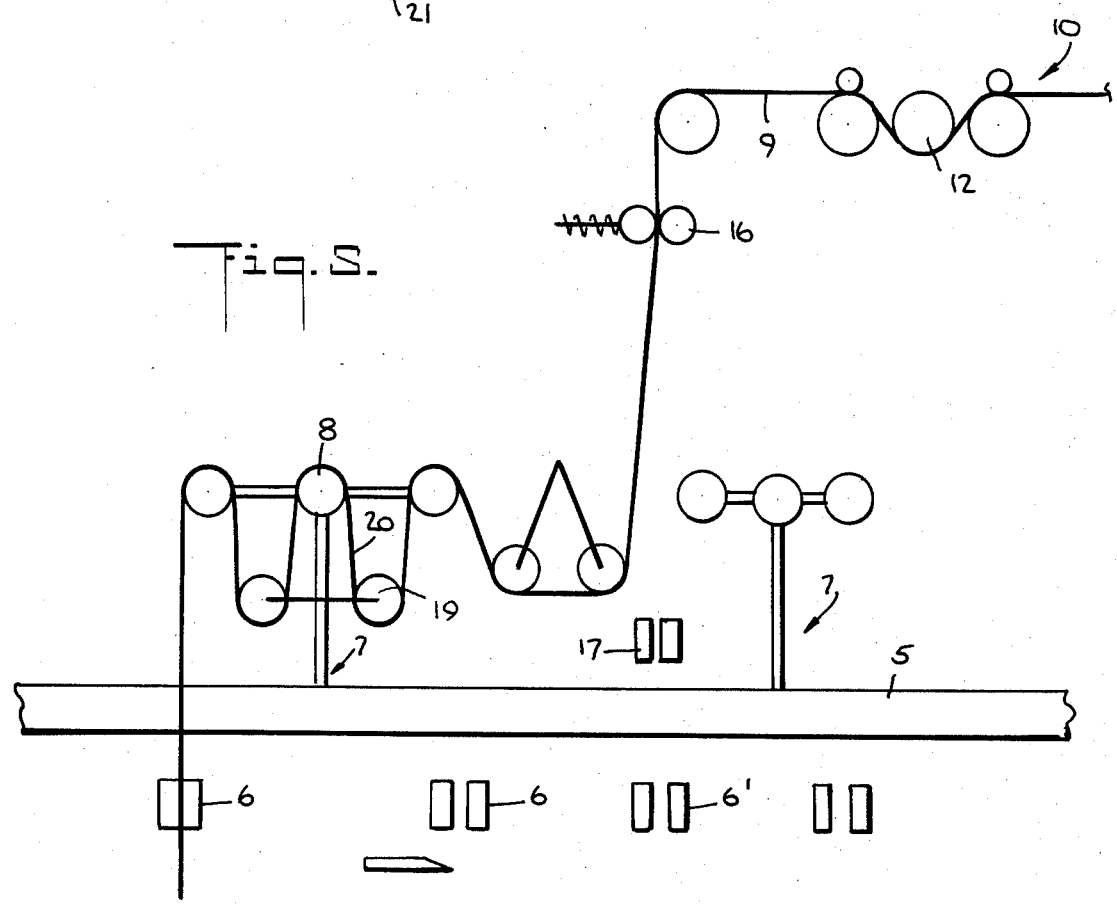
Figure 6:
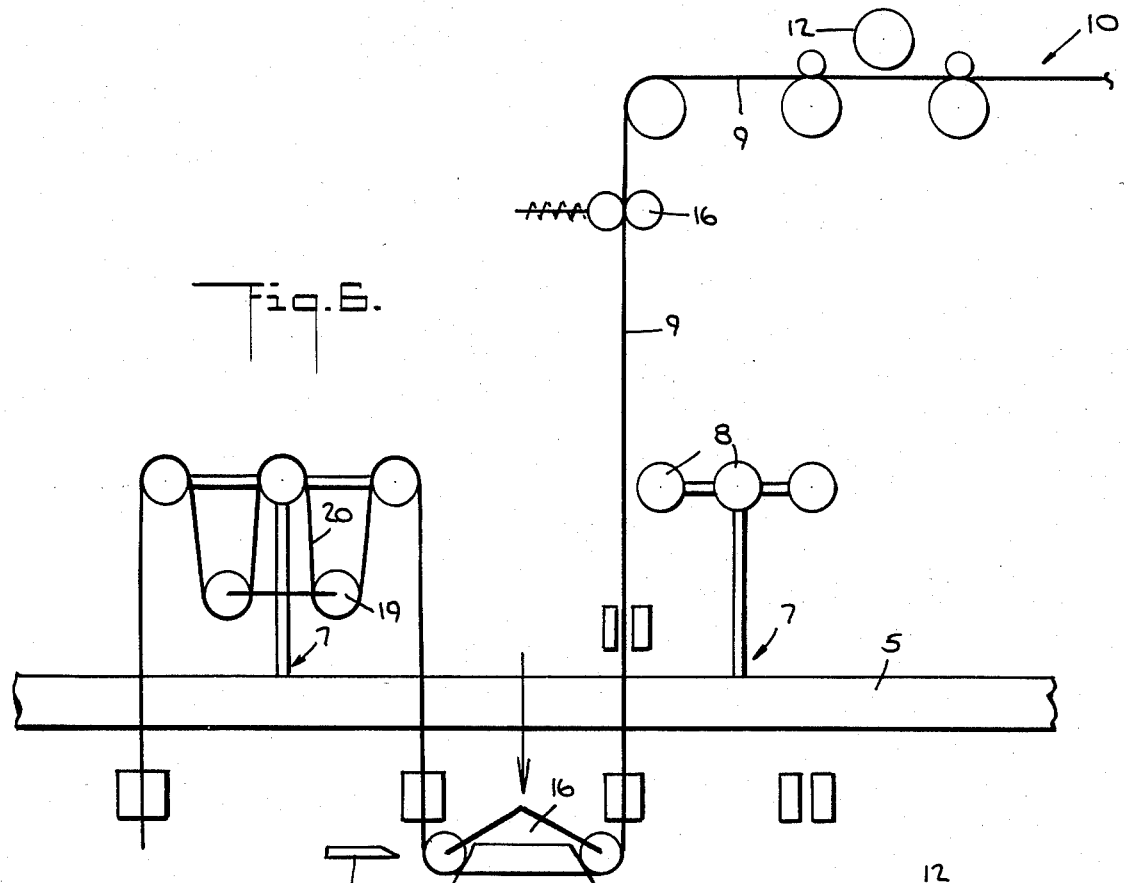
Figure 7:
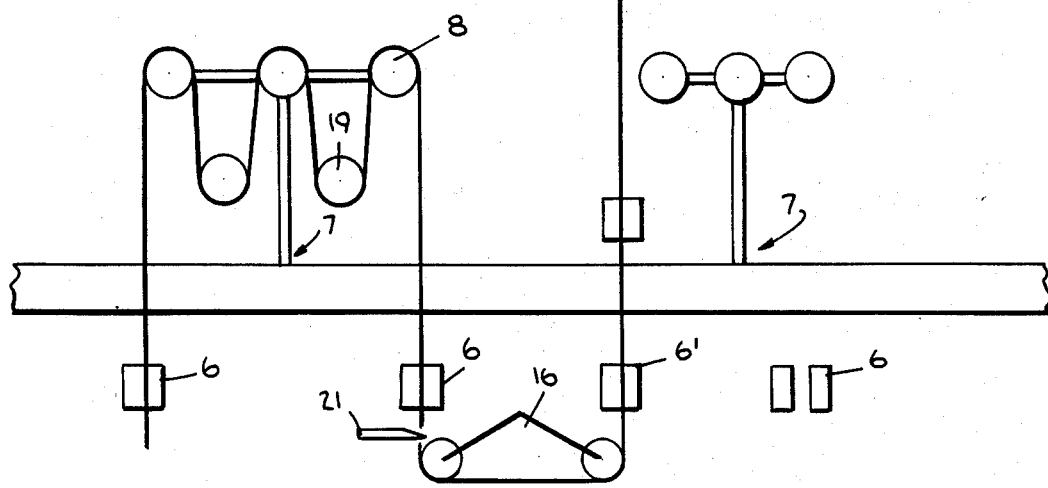

As illustrated in FIG. 5, the tube feeder assembly 16 now moves downardly drawing further tubing 9 from the rolls and the slack loop to move the tubing 9 into the right hand clamp 6 at the station A (FIG. 6). This clamp 6 closes when the feeder assembly 16 has reached its lowermost position. A cutter 21 (FIG. 7) now cuts the tube 9 as the adjacent portion is engaged by the left hand clamp 6 in the next turret station B as illustrated in FIG. 7.

Figure 10:
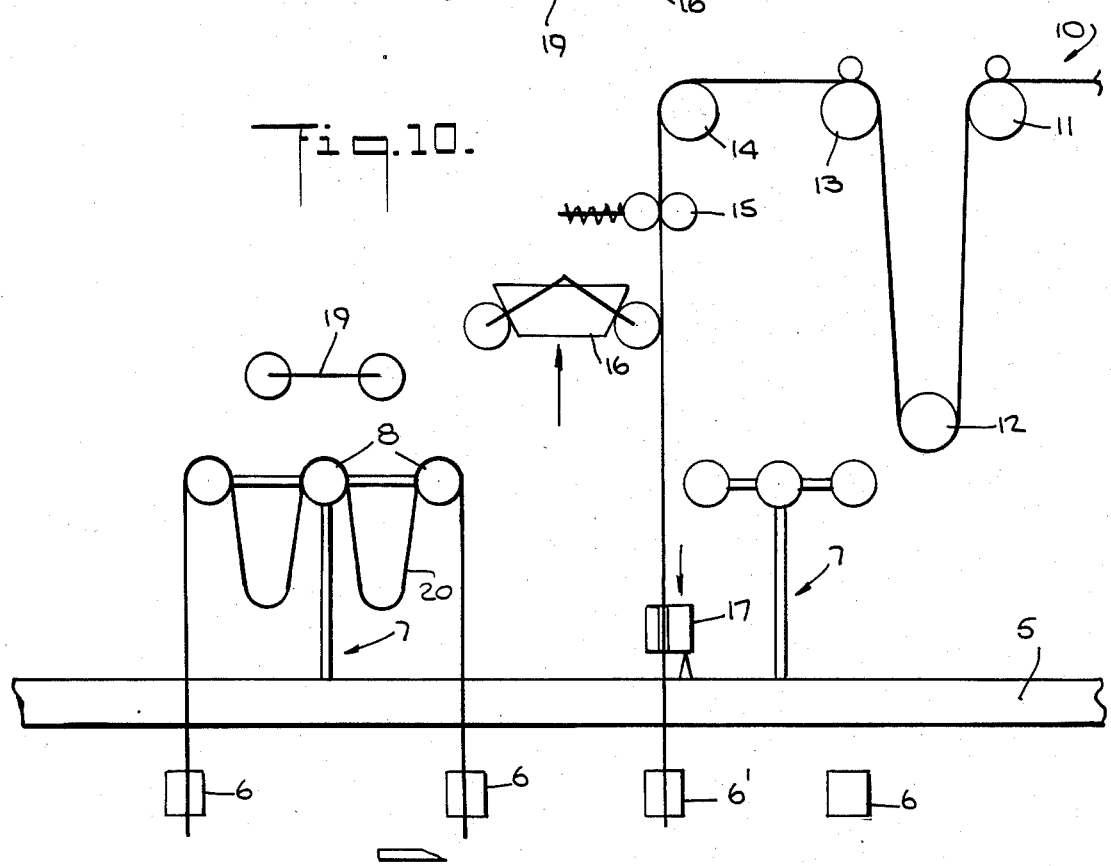

As illustrated in successive diagramatic views FIGS. 8 and 9, the clamp 6' opens slightly as left clamp 17 closes and draws the tube 9 upwardly until the cut end is returned to clamp 6' which closes. The slack forming roller 12 moves downwardly thereby drawing the raised tubing and additional tube 9 from a supply roller as needed. Clamp 17 opens and returns to its lowered position (FIG. 10). During this time, as illustrated in FIG. 9, the tube feeder assembly 16 returns to its raised initial position. The cycle is complete, as illustrated in FIG. 10, when the tube feeder assembly 16 has returned to its raised position and the slack forming roll 12 has moved to its lowermost loop forming position.

The above described elements are now ready for their next and similar cycle. A tube 1 of pre-determined length is now present on the spool assembly 8 with its opposite free ends gripped in the spaced station jaws 6. The turret 5 now steps this station past a series of stationary work stations around the periphery of the turret 5.

Various operations may now be performed on the opposite ends of the tube 1 as, for example, the application of adhesive or solvent at stations 22 permitting the opposite ends of the tubes 1 to be moved into end fixtures such as 2 and 3 presented to the two tube ends at the two spaced insert dials 23 illustrated in FIG. L. Various fixtures are placed in suitable nests in the dials 23 to receive the tube ends through a relative motion between the nests 24 and the clamped tube ends.

It will be seen that an improved automatic method and means have been described for cutting and handling short lengths of tubing.

As various changes may be made in the form, construction and arrangement of the invention and without departing from the spirit and scope of the invention, and without sacrificing any of its advantages, it is to be understood that all matter herein is to be interpreted as illustrative and not in a limiting sense.

Having thus described my invention, I claim:

1. An improved method of cutting lengths of tubing from a spool of tubing of indeterminate length and handling the cut lengths comprising the steps of:
    drawing the end of the spooled tubing generally downwardly to an end clamp;
    moving the clamped end a predetermined distance horizontally and forming a vertically hanging slack loop of predetermined tube length between the clamped end of the tubing and the spool;
    moving an intermediate portion of the tubing between said loop and spool downwardly into a second end clamp spaced from said first clamp;
    cutting the tubing at the second clamp on the roll side of the tubing thereby forming a cut tube of predetermined length clamped at its opposite ends.

2. The method as claimed in claim 1 which further comprises the step of pulling the newly cut end of the tubing backwardly to a third spaced end clamp.

3. The method as claimed in claim 2 which comprises the further step of forming a slack loop in the tubing between the tubing spool and the third end clamp.

4. The method as claimed in claim 1 which comprises the further step of forming an adhesive surface on one or both ends of said cut tube.

5. The method as claimed in claim 4 which further comprises the further step of attaching a mixture to one of said tube ends.

6. The method as claimed in claim 5 which comprises the step of attaching a fixture to the other of said tube ends.

7. An improved means for cutting lengths of tubing from a roll of tubing of indeterminate length and handling the cut lengths comprising the combination of:
    a tubing feeder;
    a tubing end clamp;
    turret means for moving the end clamp a predetermined distance and a spool assembly on said turret means for forming a slack loop of predetermined tube length between the clamped end of the tubing and the spool;
    feeder means on said turret for moving an intermediate portion of the tubing between said loop and spool into a second end clamp spaced from said first clamp;
    a second tubing end clamp;
    knife means for cutting the tubing at the second clamp on the roll side of the tubing thereby forming a cut tube of predetermined length including a slack loop clamped at its opposite ends.

8. The means as claimed in claim 7 which further comprises means for pulling the newly cut end of the tubing backwardly to a third spaced end clamp, and a third end clamp.

9. The means as claimed in claim 8 which comprises means for forming a slack loop in the tubing between the tubing spool and the third end clamp.

10. The means as claimed in claim 7 which comprises means for forming an adhesive surface on one or both ends of said cut tube.

11. The means as claimed in claim 10 which further comprises means for attaching a fixture to one of said tube ends.

12. The means as claimed in claim 10 which comprises means for attaching a fixture to the other of said tube ends.

* * * * *